US011304700B2

(12) United States Patent
Rosqueta et al.

(10) Patent No.: US 11,304,700 B2
(45) Date of Patent: *Apr. 19, 2022

(54) DEVICES, SYSTEMS, AND METHODS FOR THE TREATMENT OF VASCULAR DEFECTS

(71) Applicant: Covidien LP, Mansfield, MA (US)

(72) Inventors: Arturo Rosqueta, San Jose, CA (US); Gaurav Krishnamurthy, Mountain View, CA (US); Jose Gonzalez, Fremont, CA (US); Patrick Quinn, Oakland, CA (US); Eric Yu, San Francisco, CA (US)

(73) Assignee: COVIDIEN LP, Mansfield, MA (US)

( * ) Notice: Subject to any disclaimer, the term of this patent is extended or adjusted under 35 U.S.C. 154(b) by 241 days.

This patent is subject to a terminal disclaimer.

(21) Appl. No.: 16/738,968

(22) Filed: Jan. 9, 2020

(65) Prior Publication Data

US 2020/0138447 A1     May 7, 2020

Related U.S. Application Data

(63) Continuation of application No. 15/683,627, filed on Aug. 22, 2017, now Pat. No. 10,675,036.

(51) Int. Cl.
*A61B 17/12* (2006.01)
(52) U.S. Cl.
CPC .. *A61B 17/12113* (2013.01); *A61B 17/12163* (2013.01); *A61B 17/12172* (2013.01); *A61B 17/12177* (2013.01); *A61B 2017/1205* (2013.01)
(58) Field of Classification Search
CPC ........ A61B 17/12022; A61B 17/12031; A61B 17/12113; A61B 17/12118; A61B 17/1214; A61B 17/12145; A61B 17/12163; A61B 17/12168; A61B 17/12172; A61B 17/12177; A61B 2017/1205

See application file for complete search history.

(56) References Cited

U.S. PATENT DOCUMENTS 5,250,071 A    10/1993  Palermo
5,354,295 A    10/1994  Guglielmi et al.
(Continued)

FOREIGN PATENT DOCUMENTS

CA          2812012 A1    3/2012
DE     102011102933 A1   12/2012
(Continued)

OTHER PUBLICATIONS

European Search Report dated Feb. 5, 2021; European Patent Application No. 18849224.3; 10 pages.

*Primary Examiner* — Ryan J. Severson
(74) *Attorney, Agent, or Firm* — Fortem IP LLP; Mary Fox

(57) ABSTRACT

Devices, systems, and methods for treating vascular defects are disclosed herein. One aspect of the present technology, for example, is directed toward an occlusive device that includes a first mesh having an expanded state in which it curves about a first axis to form a first band, and a second mesh having an expanded state in which it curves about a second axis different than the first axis to form a second band. The second band may be positioned radially inward of the first band such that the device includes first and second overlap regions in which the first band overlaps the second band.

24 Claims, 7 Drawing Sheets

(56) References Cited

U.S. PATENT DOCUMENTS

| | | |
|---|---|---|
| 5,645,558 A | 7/1997 | Horton |
| 5,669,931 A | 9/1997 | Kupiecki et al. |
| 5,725,552 A | 3/1998 | Kotula et al. |
| 5,733,294 A | 3/1998 | Forber et al. |
| 5,741,333 A | 4/1998 | Frid |
| 5,749,891 A | 5/1998 | Ken et al. |
| 5,749,919 A | 5/1998 | Blanc |
| 5,814,062 A | 9/1998 | Sepetka et al. |
| 5,911,731 A | 6/1999 | Pham et al. |
| 5,916,235 A | 6/1999 | Guglielmi |
| 5,925,060 A | 7/1999 | Forber |
| 5,928,260 A | 7/1999 | Chin et al. |
| 5,935,148 A | 8/1999 | Villar et al. |
| 5,944,738 A | 8/1999 | Amplatz et al. |
| 5,951,599 A | 9/1999 | McCrory |
| 5,964,797 A | 10/1999 | Ho |
| 5,976,169 A | 11/1999 | Imran |
| 5,980,554 A | 11/1999 | Lenker et al. |
| 6,022,374 A | 2/2000 | Imran |
| 6,033,423 A | 3/2000 | Ken et al. |
| 6,036,720 A | 3/2000 | Abrams et al. |
| 6,059,812 A | 5/2000 | Clerc et al. |
| 6,063,070 A | 5/2000 | Eder |
| 6,063,104 A | 5/2000 | Villar et al. |
| 6,086,577 A | 7/2000 | Ken et al. |
| 6,090,125 A | 7/2000 | Horton |
| 6,093,199 A | 7/2000 | Brown et al. |
| 6,096,021 A | 8/2000 | Helm et al. |
| 6,123,715 A | 9/2000 | Amplatz |
| 6,139,564 A | 10/2000 | Teoh |
| 6,152,144 A | 11/2000 | Lesh et al. |
| 6,159,531 A | 12/2000 | Dang et al. |
| 6,168,615 B1 | 1/2001 | Ken et al. |
| 6,168,622 B1 | 1/2001 | Mazzocchi |
| 6,309,367 B1 | 10/2001 | Boock |
| 6,344,048 B1 | 2/2002 | Chin et al. |
| 6,346,117 B1 | 2/2002 | Greenhalgh |
| 6,350,270 B1 | 2/2002 | Roue |
| 6,368,339 B1 | 4/2002 | Amplatz |
| 6,371,980 B1 | 4/2002 | Rudakov et al. |
| 6,375,668 B1 | 4/2002 | Gifford et al. |
| 6,383,174 B1 | 5/2002 | Eder |
| 6,391,037 B1 | 5/2002 | Greenhalgh |
| 6,428,558 B1 | 8/2002 | Jones et al. |
| 6,447,531 B1 | 9/2002 | Amplatz |
| 6,451,050 B1 | 9/2002 | Rudakov et al. |
| 6,454,780 B1 | 9/2002 | Wallace |
| 6,494,884 B2 | 12/2002 | Gifford et al. |
| 6,506,204 B2 | 1/2003 | Mazzocchi |
| 6,511,468 B1 | 1/2003 | Cragg et al. |
| 6,547,804 B2 | 4/2003 | Porter et al. |
| 6,551,303 B1 | 4/2003 | Van et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,599,308 B2 | 7/2003 | Amplatz |
| 6,602,261 B2 | 8/2003 | Greene et al. |
| 6,605,101 B1 | 8/2003 | Schaefer et al. |
| 6,605,102 B1 | 8/2003 | Mazzocchi et al. |
| 6,605,111 B2 | 8/2003 | Bose et al. |
| 6,613,074 B1 | 9/2003 | Mitelberg et al. |
| 6,626,939 B1 | 9/2003 | Burnside et al. |
| 6,635,068 B1 | 10/2003 | Dubrul et al. |
| 6,652,556 B1 | 11/2003 | Vantassel et al. |
| 6,666,882 B1 | 12/2003 | Bose et al. |
| 6,669,721 B1 | 12/2003 | Bose et al. |
| 6,682,546 B2 | 1/2004 | Amplatz |
| 6,689,486 B2 | 2/2004 | Ho et al. |
| 6,730,108 B2 | 5/2004 | Van et al. |
| 6,746,468 B1 | 6/2004 | Sepetka et al. |
| 6,746,890 B2 | 6/2004 | Gupta et al. |
| 6,780,196 B2 | 8/2004 | Chin et al. |
| 6,802,851 B2 | 10/2004 | Jones et al. |
| 6,811,560 B2 | 11/2004 | Jones et al. |
| 6,855,153 B2 | 2/2005 | Saadat |
| 6,855,154 B2 | 2/2005 | Abdel-Gawwad |
| 6,878,384 B2 | 4/2005 | Cruise et al. |
| 6,905,503 B2 | 6/2005 | Gifford et al. |
| 6,936,055 B1 | 8/2005 | Ken et al. |
| 6,991,617 B2 | 1/2006 | Hektner et al. |
| 6,994,092 B2 | 2/2006 | Van et al. |
| 6,994,717 B2 | 2/2006 | Konya et al. |
| 7,011,671 B2 | 3/2006 | Welch |
| 7,029,487 B2 | 4/2006 | Greene et al. |
| 7,083,632 B2 | 8/2006 | Avellanet et al. |
| 7,128,073 B1 | 10/2006 | Van et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,229,461 B2 | 6/2007 | Chin et al. |
| 7,232,461 B2 | 6/2007 | Ramer |
| 7,326,225 B2 | 2/2008 | Ferrera et al. |
| 7,331,980 B2 | 2/2008 | Dubrul et al. |
| 7,419,503 B2 | 9/2008 | Pulnev et al. |
| 7,597,704 B2 | 10/2009 | Frazier et al. |
| 7,601,160 B2 | 10/2009 | Richter |
| 7,708,754 B2 | 5/2010 | Balgobin et al. |
| 7,879,064 B2 | 2/2011 | Monstadt et al. |
| RE42,625 E | 8/2011 | Guglielmi |
| 8,043,326 B2 | 10/2011 | Hancock et al. |
| 8,142,456 B2 | 3/2012 | Rosqueta et al. |
| 8,211,160 B2 | 7/2012 | Garrison et al. |
| 8,333,783 B2 | 12/2012 | Braun et al. |
| 8,343,167 B2 | 1/2013 | Henson |
| 8,361,104 B2 | 1/2013 | Jones et al. |
| 8,361,138 B2 | 1/2013 | Adams |
| 8,425,541 B2 | 4/2013 | Masters et al. |
| 8,444,668 B2 * | 5/2013 | Jones ................ A61B 17/1214 606/200 |
| 8,470,013 B2 | 6/2013 | Duggal et al. |
| 8,696,701 B2 * | 4/2014 | Becking ............ A61B 17/1215 606/200 |
| 8,715,317 B1 | 5/2014 | Janardhan et al. |
| 8,747,597 B2 * | 6/2014 | Rosqueta ......... A61B 17/12109 156/227 |
| 8,771,294 B2 * | 7/2014 | Sepetka ........... A61B 17/12181 606/144 |
| 8,834,515 B2 | 9/2014 | Win et al. |
| 8,864,790 B2 * | 10/2014 | Strauss .............. A61B 17/1214 606/200 |
| 8,906,057 B2 | 12/2014 | Connor et al. |
| 8,974,512 B2 | 3/2015 | Aboytes et al. |
| 8,998,947 B2 | 4/2015 | Aboytes et al. |
| 9,211,202 B2 | 12/2015 | Strother et al. |
| 9,486,224 B2 | 11/2016 | Riina et al. |
| 9,585,669 B2 * | 3/2017 | Becking ............ A61B 17/12022 |
| 9,687,245 B2 * | 6/2017 | Molaei ............. A61B 17/12113 |
| 9,713,475 B2 * | 7/2017 | Divino ............. A61B 17/12168 |
| 9,833,309 B2 | 12/2017 | Levi et al. |
| 9,844,380 B2 | 12/2017 | Furey |
| 9,844,382 B2 | 12/2017 | Aboytes et al. |
| 9,855,051 B2 | 1/2018 | Aboytes et al. |
| 9,855,052 B2 * | 1/2018 | Aboytes ............ A61B 17/1214 |
| 9,907,684 B2 | 3/2018 | Connor et al. |
| 9,962,146 B2 | 5/2018 | Hebert et al. |
| 10,028,745 B2 | 7/2018 | Morsi |
| 10,064,627 B2 * | 9/2018 | Aboytes ........... A61B 17/12168 |
| 10,111,670 B2 * | 10/2018 | Lorenzo ............ A61B 17/1214 |
| 10,130,372 B2 * | 11/2018 | Griffin ............. A61B 17/12113 |
| 2001/0000797 A1 | 5/2001 | Mazzocchi |
| 2001/0001835 A1 | 5/2001 | Greene et al. |
| 2002/0062145 A1 | 5/2002 | Rudakov et al. |
| 2002/0169473 A1 | 11/2002 | Sepetka et al. |
| 2002/0193812 A1 | 12/2002 | Patel et al. |
| 2002/0193813 A1 | 12/2002 | Helkowski et al. |
| 2003/0004533 A1 | 1/2003 | Dieck et al. |
| 2003/0004568 A1 | 1/2003 | Ken et al. |
| 2003/0018294 A1 | 1/2003 | Cox |
| 2003/0028209 A1 | 2/2003 | Teoh et al. |
| 2003/0040772 A1 | 2/2003 | Hyodoh et al. |
| 2003/0055440 A1 | 3/2003 | Jones et al. |
| 2003/0093111 A1 | 5/2003 | Ken et al. |
| 2003/0113478 A1 | 6/2003 | Dang et al. |

(56) References Cited

U.S. PATENT DOCUMENTS

| | | |
|---|---|---|
| 2003/0114918 A1 | 6/2003 | Garrison et al. |
| 2004/0064093 A1 | 4/2004 | Hektner et al. |
| 2004/0115164 A1 | 6/2004 | Pierce et al. |
| 2004/0161451 A1 | 8/2004 | Pierce et al. |
| 2004/0172056 A1 | 9/2004 | Guterman et al. |
| 2005/0085836 A1 | 4/2005 | Raymond |
| 2005/0222580 A1 | 10/2005 | Gifford et al. |
| 2005/0267511 A1 | 12/2005 | Marks et al. |
| 2005/0277978 A1 | 12/2005 | Greenhalgh |
| 2006/0034883 A1 | 2/2006 | Dang et al. |
| 2006/0052816 A1 | 3/2006 | Bates et al. |
| 2006/0064151 A1 | 3/2006 | Guterman et al. |
| 2006/0089618 A1 | 4/2006 | McFerran et al. |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0190025 A1 | 8/2006 | Lehe et al. |
| 2006/0190070 A1 | 8/2006 | Dieck et al. |
| 2006/0200234 A1 | 9/2006 | Hines |
| 2006/0206140 A1 | 9/2006 | Shaolian et al. |
| 2006/0206198 A1 | 9/2006 | Churchwell et al. |
| 2006/0206199 A1 | 9/2006 | Churchwell et al. |
| 2006/0241686 A1 | 10/2006 | Ferrera et al. |
| 2006/0247680 A1 | 11/2006 | Amplatz et al. |
| 2006/0271162 A1 | 11/2006 | Vito et al. |
| 2007/0010850 A1 | 1/2007 | Balgobin et al. |
| 2007/0083226 A1 | 4/2007 | Buiser et al. |
| 2007/0100426 A1 | 5/2007 | Rudakov et al. |
| 2007/0167876 A1 | 7/2007 | Euteneuer et al. |
| 2007/0167877 A1 | 7/2007 | Euteneuer et al. |
| 2007/0167972 A1 | 7/2007 | Euteneuer et al. |
| 2007/0175536 A1 | 8/2007 | Monetti et al. |
| 2007/0179520 A1 | 8/2007 | West |
| 2007/0185442 A1 | 8/2007 | Euteneuer et al. |
| 2007/0185443 A1 | 8/2007 | Euteneuer et al. |
| 2007/0185444 A1 | 8/2007 | Euteneuer et al. |
| 2007/0185457 A1 | 8/2007 | Euteneuer et al. |
| 2007/0191924 A1 | 8/2007 | Rudakov |
| 2007/0219619 A1 | 9/2007 | Dieck et al. |
| 2007/0276426 A1 | 11/2007 | Euteneuer |
| 2007/0276427 A1 | 11/2007 | Euteneuer |
| 2007/0282373 A1 | 12/2007 | Ashby et al. |
| 2007/0288083 A1 | 12/2007 | Hines |
| 2008/0082176 A1 | 4/2008 | Slazas |
| 2008/0097508 A1* | 4/2008 | Jones ............... A61B 17/12172 606/191 |
| 2008/0114391 A1 | 5/2008 | Dieck et al. |
| 2008/0114436 A1 | 5/2008 | Dieck et al. |
| 2008/0125852 A1 | 5/2008 | Garrison et al. |
| 2008/0195139 A1* | 8/2008 | Donald ............ A61B 17/12172 606/200 |
| 2008/0200945 A1 | 8/2008 | Amplatz et al. |
| 2008/0200979 A1 | 8/2008 | Dieck et al. |
| 2008/0221600 A1 | 9/2008 | Dieck et al. |
| 2008/0281350 A1 | 11/2008 | Sepetka et al. |
| 2009/0043375 A1 | 2/2009 | Rudakov et al. |
| 2009/0062841 A1 | 3/2009 | Amplatz et al. |
| 2009/0062899 A1 | 3/2009 | Dang et al. |
| 2009/0112251 A1 | 4/2009 | Qian et al. |
| 2009/0187214 A1 | 7/2009 | Amplatz et al. |
| 2009/0264978 A1 | 10/2009 | Dieck et al. |
| 2009/0275974 A1 | 11/2009 | Marchand et al. |
| 2009/0287291 A1 | 11/2009 | Becking et al. |
| 2009/0287292 A1 | 11/2009 | Becking et al. |
| 2009/0287294 A1 | 11/2009 | Rosqueta et al. |
| 2009/0297582 A1 | 12/2009 | Meyer et al. |
| 2009/0318892 A1 | 12/2009 | Aboytes et al. |
| 2009/0318941 A1 | 12/2009 | Sepetka et al. |
| 2009/0319023 A1 | 12/2009 | Hildebrand et al. |
| 2010/0030200 A1 | 2/2010 | Strauss et al. |
| 2010/0036410 A1 | 2/2010 | Krolik et al. |
| 2010/0139465 A1 | 6/2010 | Christian et al. |
| 2010/0144895 A1 | 6/2010 | Porter |
| 2010/0174269 A1 | 7/2010 | Tompkins et al. |
| 2010/0185271 A1 | 7/2010 | Zhang |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0262014 A1 | 10/2010 | Huang |
| 2010/0268201 A1 | 10/2010 | Tieu et al. |
| 2011/0022149 A1 | 1/2011 | Cox et al. |
| 2011/0046658 A1 | 2/2011 | Connor et al. |
| 2011/0077620 A1 | 3/2011 | Debeer |
| 2011/0137332 A1 | 6/2011 | Sepetka et al. |
| 2011/0137405 A1 | 6/2011 | Wilson et al. |
| 2011/0144669 A1 | 6/2011 | Becking et al. |
| 2011/0152993 A1 | 6/2011 | Marchand et al. |
| 2011/0202085 A1 | 8/2011 | Loganathan et al. |
| 2011/0208227 A1 | 8/2011 | Becking |
| 2011/0224776 A1 | 9/2011 | Sepetka et al. |
| 2011/0265943 A1 | 11/2011 | Rosqueta et al. |
| 2011/0319926 A1 | 12/2011 | Becking et al. |
| 2012/0022572 A1 | 1/2012 | Braun et al. |
| 2012/0041472 A1 | 2/2012 | Tan et al. |
| 2012/0101510 A1 | 4/2012 | Lenker et al. |
| 2012/0116350 A1 | 5/2012 | Strauss et al. |
| 2012/0165919 A1 | 6/2012 | Cox et al. |
| 2012/0197283 A1 | 8/2012 | Marchand et al. |
| 2012/0239074 A1 | 9/2012 | Aboytes et al. |
| 2012/0283769 A1 | 11/2012 | Cruise et al. |
| 2012/0316598 A1 | 12/2012 | Becking et al. |
| 2012/0316632 A1 | 12/2012 | Gao |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0116722 A1 | 5/2013 | Aboytes et al. |
| 2013/0253572 A1 | 9/2013 | Molaei et al. |
| 2013/0274866 A1 | 10/2013 | Cox et al. |
| 2014/0012307 A1 | 1/2014 | Franano et al. |
| 2014/0058420 A1 | 2/2014 | Hannes et al. |
| 2014/0316012 A1 | 10/2014 | Freyman et al. |
| 2014/0371734 A1 | 12/2014 | Truckai |
| 2015/0182227 A1 | 7/2015 | Le et al. |
| 2015/0209050 A1* | 7/2015 | Aboytes ............ A61B 17/12113 606/191 |
| 2015/0216684 A1 | 8/2015 | Enzmann et al. |
| 2015/0250628 A1 | 9/2015 | Monstadt et al. |
| 2015/0272590 A1 | 10/2015 | Aboytes et al. |
| 2015/0297240 A1 | 10/2015 | Divino et al. |
| 2015/0313737 A1 | 11/2015 | Tippett et al. |
| 2015/0327843 A1 | 11/2015 | Garrison |
| 2015/0342613 A1 | 12/2015 | Aboytes et al. |
| 2016/0022445 A1 | 1/2016 | Ruvalcaba et al. |
| 2016/0066921 A1 | 3/2016 | Seifert et al. |
| 2016/0135984 A1 | 5/2016 | Rudakov et al. |
| 2016/0206320 A1 | 7/2016 | Connor |
| 2016/0206321 A1 | 7/2016 | Connor |
| 2016/0262766 A1 | 9/2016 | Aboytes et al. |
| 2016/0317158 A1* | 11/2016 | Lorenzo ........... A61B 17/12145 |
| 2017/0150971 A1 | 6/2017 | Hines |
| 2017/0156903 A1 | 6/2017 | Shobayashi |
| 2017/0189035 A1 | 7/2017 | Porter |
| 2017/0224350 A1 | 8/2017 | Shimizu et al. |
| 2017/0266023 A1 | 9/2017 | Thomas |
| 2017/0281194 A1* | 10/2017 | Divino ............. A61B 17/12168 |
| 2017/0340333 A1 | 11/2017 | Badruddin et al. |
| 2017/0367708 A1 | 12/2017 | Mayer et al. |
| 2018/0036012 A1 | 2/2018 | Aboytes et al. |
| 2018/0049859 A1 | 2/2018 | Stoppenhagen et al. |
| 2018/0125501 A1* | 5/2018 | Aboytes ........... A61B 17/12031 |
| 2018/0125686 A1 | 5/2018 | Lu |
| 2018/0132859 A1* | 5/2018 | Aboytes ........... A61B 17/12172 |
| 2018/0132862 A1* | 5/2018 | Aboytes ........... A61B 17/12163 |
| 2018/0140305 A1 | 5/2018 | Connor |

(56) References Cited

U.S. PATENT DOCUMENTS

| | | |
|---|---|---|
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2019/0053811 A1 | 2/2019 | Garza et al. |
| 2019/0059907 A1* | 2/2019 | Rosqueta ......... A61B 17/12172 |
| 2020/0138447 A1* | 5/2020 | Rosqueta ......... A61B 17/12172 |

FOREIGN PATENT DOCUMENTS

| | | |
|---|---|---|
| EP | 0717969 A2 | 6/1996 |
| EP | 1295563 A1 | 3/2003 |
| EP | 1813213 A2 | 8/2007 |
| EP | 2208483 A1 | 7/2010 |
| EP | 2609888 A1 | 7/2013 |
| EP | 2890306 A2 | 7/2015 |
| FR | 2890306 A1 | 3/2007 |
| JP | 2005261951 A | 9/2005 |
| JP | 2008521492 A | 6/2008 |
| JP | 2010523260 A | 7/2010 |
| WO | 9406502 A2 | 3/1994 |
| WO | 9409705 A1 | 5/1994 |
| WO | 9907294 A1 | 2/1999 |
| WO | 9929260 A2 | 6/1999 |
| WO | 0164112 A1 | 9/2001 |
| WO | 02054980 A2 | 7/2002 |
| WO | 02089863 A1 | 11/2002 |
| WO | 2005099634 A1 | 10/2005 |
| WO | 2006034149 A2 | 3/2006 |
| WO | 2007121405 A2 | 10/2007 |
| WO | 2008036156 A1 | 3/2008 |
| WO | 2008074027 A1 | 6/2008 |
| WO | 2009014528 A1 | 1/2009 |
| WO | 2010009019 A1 | 1/2010 |
| WO | 2010027363 A1 | 3/2010 |
| WO | 2010077599 A1 | 7/2010 |
| WO | 2011066962 A1 | 6/2011 |
| WO | 2011095966 A1 | 8/2011 |
| WO | 2012034135 A1 | 3/2012 |
| WO | 2013112944 A1 | 8/2013 |
| WO | 2013138615 A2 | 9/2013 |
| WO | 2014105932 A1 | 7/2014 |
| WO | 2013138615 A3 | 9/2014 |
| WO | 2017074411 A1 | 5/2017 |
| WO | 2018051187 A1 | 3/2018 |

\* cited by examiner

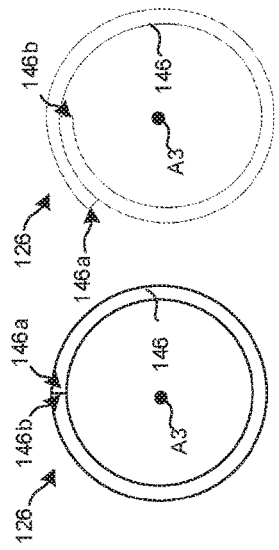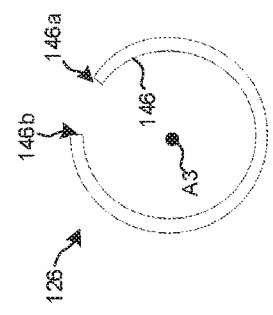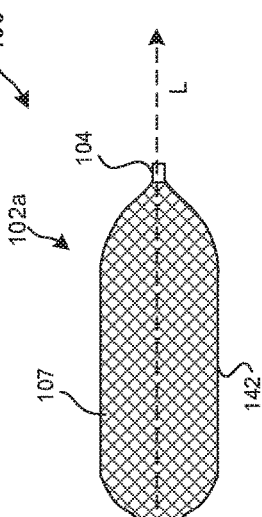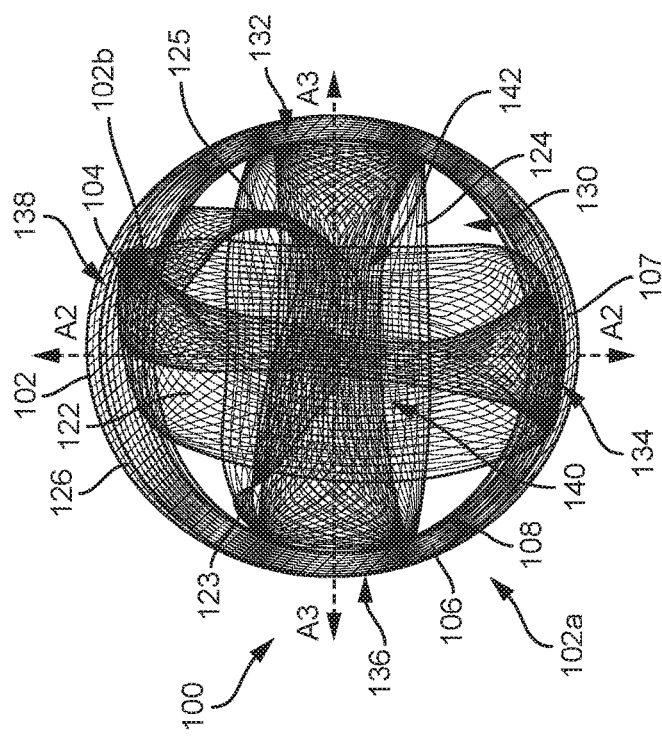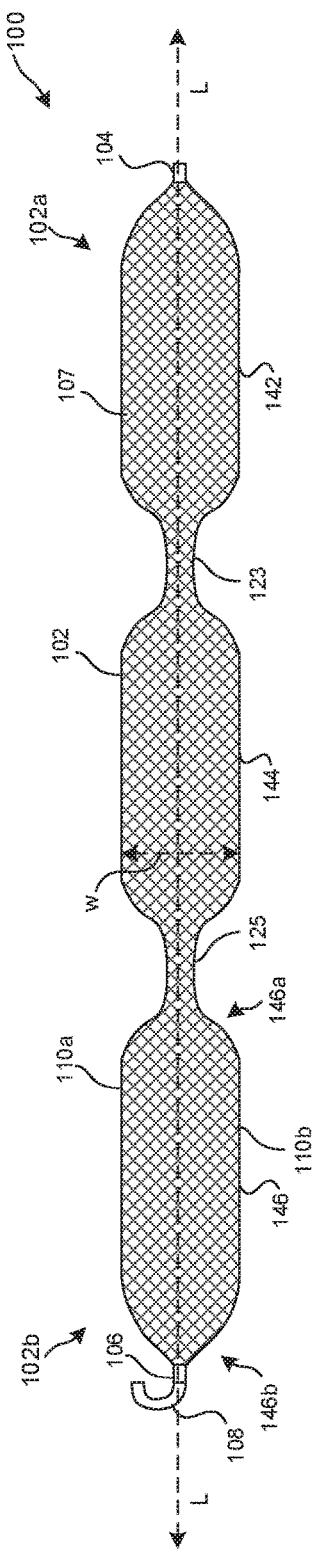

DEVICES, SYSTEMS, AND METHODS FOR THE TREATMENT OF VASCULAR DEFECTS

CROSS-REFERENCE TO RELATED APPLICATION

This application is a continuation of U.S. patent application Ser. No. 15/683,627 filed Aug. 22, 2017, which is incorporated herein by reference in its entirety.

TECHNICAL FIELD

The present technology is directed generally to devices, systems, and methods for the treatment of vascular defects.

BACKGROUND

Aneurysms are blood-filled dilations of a blood vessel generally caused by disease or weakening of the blood vessel wall. The wall of the aneurysm may progressively thin, which increases the risk of rupture causing hemorrhagic stroke or even sudden death. There are about 30,000 to 40,000 cases of aneurysmal rupture per year in the United States, accounting for about 5% of all strokes. The prognosis after aneurysmal rupture is poor; the 30-day mortality rate is approximately 45% and a positive functional outcome is achieved in only 40-50% of survivors. Traditional approaches to preventing aneurysmal rupture often include packing the aneurysm with metal coils to reduce the inflow of blood to the aneurysm and prevent further enlargement and rupture. Such coils are often referred to as "embolic coils" or "microcoils," and can be categorized into the following three groups based on their structural properties: framing coils, filling coils, and finishing coils. Framing coils are inserted first into the aneurysm and form the base structure into which the later-delivered filling coils are packed. As such, framing coils are stiffer than filling and finishing coils to provide structural stability and generally have a complex or three-dimensional shape for approximating the periphery of the aneurysm. Filling coils, in contrast, are softer than framing coils, and multiple filling coils are packed within the framework of the framing coil(s) to achieve a high packing density. Finishing coils are delivered last to fill any remaining gaps left between filling coils.

Embolic coils, however, have several drawbacks. First, embolic coils generally only achieve a 20-40% packing density (i.e., ratio of the volume of the coils inserted into the aneurysm sac and the volume of the aneurysm sac). As a result, blood continues to flow into the aneurysm (also known as recanalization) in about 30% of coil cases, which can cause further swelling of the aneurysm over time. In addition, because the coils must be very small to fit within a microcatheter for delivery through the tiny cranial vessels, numerous coils are often required to adequately fill the aneurysm. These numerous coils must be delivered one-by-one, thereby increasing procedure time and complexity. Yet another drawback is that embolic coils cannot accommodate the wide range of aneurysm shapes and sizes. Embolic coils, for example, are difficult to stabilize within wide-necked aneurysms, which can result in migration of one or more coils across the neck such that a portion of the migrated coil(s) protrudes into the parent blood vessel. The protruding portion of the migrated coil(s) can be a nidus for thromboembolism, which can be fatal if left unaddressed. To address this shortcoming, many existing treatments include positioning an intracranial stent across the neck of the aneurysm to prevent all or part of a coil from migrating across the neck. However, intracranial stents can also be a nidus for thromboembolism, and further increase procedure time and cost. Thus, there is a need for improved devices, systems, and methods for treating aneurysms.

SUMMARY

The present technology is directed generally to devices, systems, and methods for the treatment of vascular defects, and in particular, to vascular occlusion devices for treating hemorrhagic stroke. In some embodiments, the present technology includes an expandable occlusion device comprising a mesh structure having a low-profile state for intravascular delivery to an aneurysm and an expanded state in which the mesh is configured to be positioned within the interior cavity of the aneurysm. As used herein, "mesh" or "mesh structure" may refer to a stent, a braid, a lattice, a weave, a laser-cut sheet, and/or any other suitable porous structures. In some embodiments, the occlusion device includes a mesh structure having two or more mesh portions that have different shapes and/or configurations. The mesh portions complement one another when positioned together within the aneurysm to stabilize and/or anchor the mesh within the aneurysm, fill space within the aneurysm, and/or seal the neck of the aneurysm to prevent or reduce blood flow therethrough.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause [1, 17, and 31]. The other clauses can be presented in a similar manner.

Clause 1. An occlusive device for treating an aneurysm, wherein a neck of the aneurysm opens to a blood vessel, the device comprising:
  a first elongated mesh having a low-profile state for intravascular delivery to the aneurysm and an expanded state in which the first elongated mesh is curved about a first axis to form a first band; and
  a second elongated mesh having a low-profile state for intravascular delivery to the aneurysm and an expanded state in which the second elongated mesh is curved about a second axis different than the first axis to form a second band, wherein the second band is positioned radially inward of the first band such that the device includes first and second overlap regions in which the first band overlaps the second band, and wherein the first and second overlap regions are spaced apart from one another along a circumference of the first band.

Clause 2. The device of Clause 1, wherein the first and second elongated meshes are self-expanding.

Clause 3. The device of Clause 1 or Clause 2, wherein the first and second bands together bound a generally spherical shape, and wherein the first and second bands conform to an interior geometry of the aneurysm when the device is positioned within the aneurysm.

Clause 4. The device of any one of Clauses 1-3, wherein the device is configured to be positioned in the aneurysm in an expanded state such that the first or second overlap region is positioned at the neck of the aneurysm, thereby substantially covering the neck and reducing blood flow through the neck from a parent vessel.

Clause 5. The device of any one of Clauses 1-4, wherein the first axis is generally perpendicular to the second axis.

Clause 6. The device of any one of Clauses 1-5, wherein each of the first and second bands have a generally constant width along their respective circumferential lengths.

Clause 7. The device of any one of Clauses 1-6, further comprising a third elongated mesh having a low-profile state for intravascular delivery to the aneurysm and an expanded state in which the third elongated mesh is curved about a third axis different than the first axis and the second axis to form a third band.

Clause 8. The device of any one of Clauses 1-7, wherein at least one of the first elongated mesh and the second elongated mesh is a braid.

Clause 9. The device of any one of Clauses 1-8, wherein at least one of the first elongated mesh and the second elongated mesh is a flattened tubular braid.

Clause 10. The device of any one of Clauses 1-9, wherein the device includes a flexible joint between a distal end of the first elongated mesh and a proximal end of the second elongated mesh.

Clause 11. The device of Clause 10, wherein the first elongated mesh and the second elongated mesh are formed of a single, continuous elongated mesh, and wherein the joint is a narrowed region of the mesh configured to direct a proximal portion of the second elongated mesh away from the first band when the device is in an expanded state.

Clause 12. The device of Clause 10, wherein the first elongated mesh and second elongated mesh are discrete, separate meshes, and wherein the joint is a coupler.

Clause 13. The device of any one of Clauses 1-12, wherein the first and second elongated meshes have at least two layers such that the first and second overlap regions of the device include at least four mesh layers.

Clause 14. The device of any one of Clauses 1-13, wherein a proximal end of the first elongated mesh is configured to be detachably coupled to an elongated delivery member.

Clause 15. The device of any one of Clauses 1-14, wherein a distal end of the second elongated mesh is coupled to an atraumatic lead-in member that extends distally from the second elongated mesh.

Clause 16. The device of any one of Clauses 1-15, wherein the device includes a plurality of openings between the first and second elongated meshes.

Clause 17. The device of any one of Clauses 1-16, wherein:
the first and second bands together bound a predetermined, three-dimensional shape,
the first elongated mesh has first longitudinal side edges,
the second elongated mesh is bound by second longitudinal side edges, and
when the device is in the expanded state, the first and the second side edges are spaced apart from one another along at least a portion of their circumferential lengths such that the device includes openings at its outer surface.

Clause 18. The device of any one of Clauses 1-16, wherein:
the first and second bands together bound a predetermined, three-dimensional shape,
the first elongated mesh has first longitudinal side edges,
the second elongated mesh is bound by second longitudinal side edges, and
when the device is in the expanded state, the first and the second side edges contact one another along at least a portion of their circumferential lengths and/or overlap one another along at least a portion of their circumferential lengths such that the first and second bands define a continuous outer surface of the three-dimensional shape.

Clause 19. The device of any one of Clauses 1-18, wherein, in the expanded state, the first band is an open band such that when the first band is viewed in cross section, it does not form a closed shape.

Clause 20. The device of any one of Clauses 1-19, wherein, in the expanded state, the second band is an open band such that when the second band is viewed in cross section, it does not form a closed shape.

Clause 21. The device of any one of Clauses 1-18 and 20, wherein, in the expanded state, the first band is a closed band such that when the first band is viewed in cross section, it forms a closed shape.

Clause 22. The device of any one of Clauses 1-19 and 21, wherein, in the expanded state, the second band is a closed band such that when the second band is viewed in cross section, it forms a closed shape.

Clause 23. The device of any one of Clauses 1-22, wherein the first and second bands together bound a predetermined, three-dimensional shape.

Clause 24. An occlusive device for treating an aneurysm, wherein a neck of the aneurysm opens to a blood vessel, the device comprising:
a first elongated mesh strip having a low-profile state for intravascular delivery to the aneurysm and an expanded state in which the first elongated mesh strip is curved about a first axis to form a first band encircling at least a portion of a first opening;
a second elongated mesh strip having a low-profile state for intravascular delivery to the aneurysm and an expanded state in which the second elongated mesh strip is curved about a second axis to form a second band encircling at least a portion of a second opening; and
a third elongated mesh strip having a low-profile state for intravascular delivery to the aneurysm and an expanded state in which the third elongated mesh strip is curved about a third axis to form a third band encircling at least a portion of a third opening,
wherein, when the device is in an expanded, unconstrained state, the first, second, and third openings are aligned with first, second, and third planes, respectively, and the first second and third planes are perpendicular to one another.

Clause 25. The device of Clause 24, wherein the first, second, and third elongated mesh strips are self-expanding.

Clause 26. The device of any one of Clause 24 or Clause 25, wherein the first, second, and third bands together bound a generally spherical shape, and wherein the first, second, and third bands conform to an interior geometry of the aneurysm when the device is positioned within the aneurysm.

Clause 27. The device of any one of Clauses 24-26, wherein the device includes:
first and second overlap regions in which the first band intersects the second band;
third and fourth overlap regions in which the first band intersects the third band; and
fifth and sixth overlap regions in which the second band intersects the third band.

Clause 28. The device of Clause 27, wherein the device is configured to be positioned in the aneurysm in an expanded state such that at least one of the first-sixth overlap regions are positioned at the neck of the aneurysm, thereby substantially covering the neck and reducing blood flow from a parent vessel through the neck.

Clause 29. The device of any one of Clauses 24-28, wherein at least one of the first, second, and third elongated mesh strips is a braid.

Clause 30. The device of any one of Clauses 24-29, wherein at least one of the first, second, and third elongated mesh strips is a flattened tubular braid.

Clause 31. The device of any one of Clauses 24-30, wherein a distal end of the first elongated mesh strip is coupled to a proximal end of the second elongated mesh strip at a first joint, and a distal end of the second elongated mesh strip is coupled to a proximal end of the third elongated mesh strip at a second joint.

Clause 32. The device of any one of Clauses 24-31, wherein the third elongated mesh is configured to be released from a delivery catheter before the second elongated mesh, and the second elongated mesh is configured to be released from a delivery catheter before the first elongated mesh.

Clause 33. The device of any one of Clauses 24-32, wherein a proximal end of the first elongated mesh strip is configured to be detachably coupled to an elongated delivery member.

Clause 34. The device of any one of Clauses 24-33, wherein a distal end of the third elongated mesh strip is coupled to an atraumatic lead-in member that extends distally from the third elongated mesh.

Clause 35. The device of any one of Clauses 24-34, wherein, when the device is in an expanded, unconstrained state, the third band is radially inward of the second band, and the second band is radially inward of the first band.

Clause 36. The device of any one of Clauses 24-35, wherein the first, second, and third elongated mesh strips are formed of a single, continuous elongated mesh.

Clause 37. The device of any one of Clauses 24-35, wherein the first, second, and third elongated mesh strips are discrete, separate meshes.

Clause 38. The device of any one of Clauses 24-37, wherein:
the first, second, and third bands together bound a predetermined, three-dimensional shape,
the first elongated mesh has first longitudinal side edges,
the second elongated mesh is bound by second longitudinal side edges,
the third elongated mesh is bound by third longitudinal side edges, and
when the device is in the expanded state, the first, second, and third side edges are spaced apart from one another along at least a portion of their circumferential lengths such that the device includes openings at its outer surface.

Clause 39. The device of any one of Clauses 24-37, wherein:
the first, second, and third bands together bound a predetermined, three-dimensional shape,
the first elongated mesh has first longitudinal side edges,
the second elongated mesh is bound by second longitudinal side edges, and
when the device is in the expanded state, the first and the second side edges contact one another along at least a portion of their circumferential lengths and/or overlap one another along at least a portion of their circumferential lengths such that the first, second, and third bands define a continuous outer surface of the three-dimensional shape.

Clause 40. The device of any one of Clauses 24-39, wherein, in the expanded state, the first band is an open band such that when the first band is viewed in cross section, it does not form a closed shape.

Clause 41. The device of any one of Clauses 24-40, wherein, in the expanded state, the second band is an open band such that when the second band is viewed in cross section, it does not form a closed shape.

Clause 42. The device of any one of Clauses 24-41, wherein, in the expanded state, the third band is an open band such that when the third band is viewed in cross section, it does not form a closed shape.

Clause 43. The device of any one of Clauses 24-39, 41, or 42, wherein, in the expanded state, the first band is a closed band such that when the first band is viewed in cross section, it forms a closed shape.

Clause 44. The device of any one of Clauses 24-40, 42, or 43, wherein, in the expanded state, the second band is a closed band such that when the second band is viewed in cross section, it forms a closed shape.

Clause 45. The device of any one of Clauses 24-41, 43, or 44, wherein, in the expanded state, the third band is a closed band such that when the third band is viewed in cross section, it forms a closed shape.

Clause 46. The device of any one of Clauses 24-45, wherein the first, second, and third bands together bound a predetermined, three-dimensional shape.

Clause 47. A method for treating an aneurysm with an occlusive device including a first elongated mesh and a second elongated mesh, wherein a neck of the aneurysm opens to a blood vessel, the method comprising:
pushing the first elongated mesh distally from a delivery catheter into an interior region of the aneurysm, wherein pushing the first elongated mesh distally includes curving the first elongated mesh back on itself to form a first band that expands against and conforms to an inner surface of the aneurysm wall;
pushing a second elongated mesh distally from the delivery catheter into the interior region of the aneurysm, wherein pushing the second elongated mesh distally includes curving the second elongated mesh back on itself to form a second band that expands against and conforms to the inner surface of the aneurysm wall, wherein the first and second bands intersect at first and second overlap regions when the device is in an expanded state; and
positioning the device within the aneurysm such that the first or second overlap region is positioned at the neck of the aneurysm, thereby substantially covering the neck and reducing blood flow from a parent vessel through the neck.

Clause 48. The method of Clause 47, wherein the first elongated mesh is pushed distally from the delivery catheter before the second elongated mesh is pushed distally from the delivery catheter.

Clause 49. The method of Clause 47 or Clause 48, wherein:
curving the first elongated mesh back on itself to form a first band includes curving the first elongated mesh around a first axis; and
curving the second elongated mesh back on itself to form a second band includes curving the second elongated mesh around a second axis different than the first axis.

Clause 50. The method of Clause 49, wherein the first axis is perpendicular to the second axis.

Clause 51. The method of any one of Clauses 47-50, wherein the first and second elongated meshes are formed of a single, continuous elongated mesh.

Clause 52. The method of any one of Clauses 47-50, wherein the first and second elongated meshes are discrete, separate meshes.

Clause 53. The method of any one of Clauses 47-52, further comprising pushing a third elongated mesh distally from the delivery catheter into the interior region of the aneurysm, wherein pushing the third elongated mesh distally includes curving the third elongated mesh back on itself to form a third band that expands against and conforms to the inner surface of the aneurysm wall.

Clause 54. The method of Clause 53, wherein the third band is an open band.

Clause 55. The method of Clause 53, wherein the third band is a closed band.

Clause 56. The method of any one of Clauses 53-55, wherein:
the first band intersects the third band at third and fourth overlap regions of the device, and
the second band intersects the third band at fifth and sixth overlap regions of the device.

Clause 57. The method of Clause 56, further comprising positioning the device within the aneurysm such that one or more of the first-sixth overlap regions are positioned at the neck of the aneurysm.

Clause 58. The method of any one of Clauses 53-57, wherein:
curving the first elongated mesh back on itself to form a first band includes curving the first elongated mesh around a first axis;
curving the second elongated mesh back on itself to form a second band includes curving the second elongated mesh around a second axis different than the first axis; and
curving the third elongated mesh back on itself to form a third band includes curving the third elongated mesh around a third axis different than the first and second axes.

Clause 59. The method of Clause 58, wherein the first, second, and third axes are perpendicular to one another.

Clause 60. The method of any one of Clauses 47-59, wherein the first band is an open band.

Clause 61. The method of any one of Clauses 47-59, wherein the first band is a closed band.

Clause 62. The method of any one of Clauses 47-61, wherein the second band is an open band.

Clause 63. The method of any one of Clauses 47-61, wherein the second band is a closed band.

Clause 64. A method for treating an aneurysm comprising positioning any one of the occlusive devices of Clauses 1-46 within an aneurysm.

Clause 64. A method for treating an aneurysm comprising positioning two or more of the occlusive devices of Clauses 1-46 within an aneurysm, in succession.

BRIEF DESCRIPTION OF THE DRAWINGS

FIG. 1A is an occlusion device in a deployed, relaxed state outside of an aneurysm according to some embodiments of the present technology.

FIG. 1B is a top view of the occlusion device shown in FIG. 1A, unfurled and held in an elongated configuration.

FIGS. 1C-1E are schematic representations of different band configurations according to some embodiments of the present technology.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology may be practiced without these specific details.

Figure 1F:
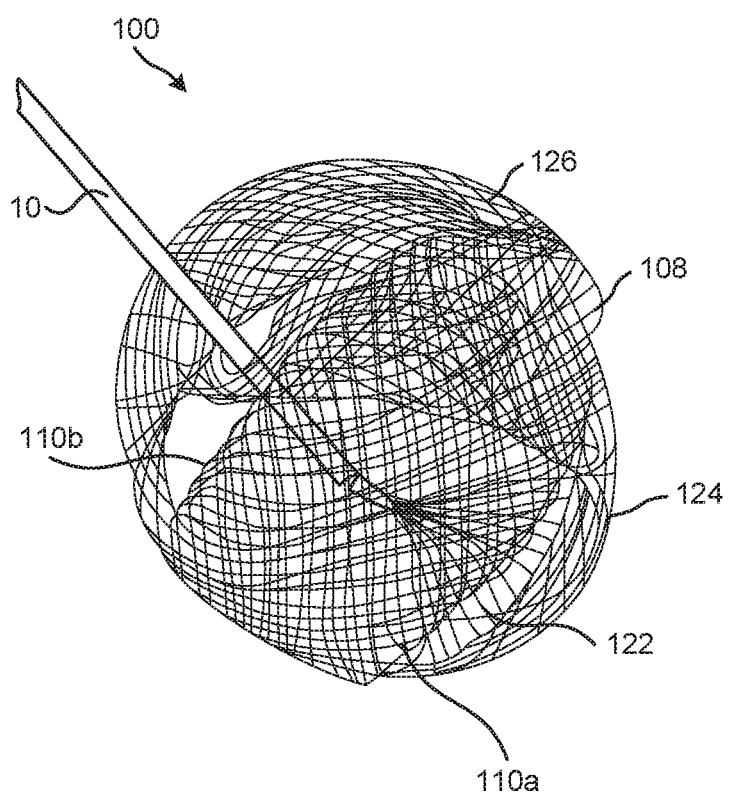
FIG. 1F is a different view of the occlusion device of FIG. 1A in a deployed, relaxed state outside of an aneurysm and coupled to a delivery member according to some embodiments of the present technology.

FIG. 1A shows an occlusion device 100 in accordance with some embodiments of the present technology shown in an expanded, relaxed configuration outside of an aneurysm. FIG. 1F is a different view of the occlusion device 100 of FIG. 1A coupled to a delivery member 10. As shown in FIGS. 1A and 1F, the occlusion device 100 may comprise a mesh structure 102 having a low-profile state (not shown) for intravascular delivery to an aneurysm (e.g., a cerebral aneurysm) and an expanded state in which the mesh structure 102 is configured to be positioned within the interior cavity of the aneurysm. In the expanded state, the mesh structure 102 may include a plurality of interconnected, nested bands 122, 124, 126 that together define a predetermined three-dimensional shape, such as the spherical shape shown in FIG. 1A. Depending on the geometry of the aneurysm to be treated, the predetermined shape delimited by the bands 122, 124, 126 can be selected from a variety of spherical or non-spherical shapes, including cylinders, hemispheres, noodles, polyhedrons (e.g., cuboids, tetrahedrons (e.g. pyramids), octahedrons, prisms, etc.), prolate spheroids, oblate spheroids, plates (e.g., discs, polygonal plates), bowls, non-spherical surfaces of revolution (e.g., toruses, cones, cylinders, or other shapes rotated about a center point or a coplanar axis), and combinations thereof In FIG. 1A, the mesh structure 102 includes three bands (referred to as first, second, and third bands 122, 124, 126). In some embodiments, the mesh structure 102 can have more or fewer than three bands (e.g., two bands, four bands, five bands, six bands, etc.).

FIG. 1B is a top view of the occlusion device 100 after being unfurled from the deployed, relaxed configuration shown in FIG. 1A and held in an unfurled, elongated configuration to provide a better view of the entire length of the occlusion device 100. Referring to FIGS. 1A and 1B together, in some embodiments the mesh structure 102 can be formed of a single, continuous mesh ribbon 107 such that each of the bands 122, 124, 126 is formed of a different portion of the ribbon 107. In some embodiments, the bands 122, 124, 126 are formed of separate meshes and are joined end-to-end by one or more coupling elements. As best shown in FIG. 1B, the mesh ribbon 107 has a proximal end portion 102a, a distal end portion 102b, a longitudinal axis L extending between the proximal and distal end portions 102a, 102b, and side edges 110a and 110b extending longitudinally between the proximal and distal end portions 102a, 102b. In some embodiments, such as that shown in FIGS. 1A and 1B, the occlusion device 100 includes a proximal connector 104 and a distal connector 106 coupled to the proximal and distal end portions 102a, 102b, respectively, of the mesh ribbon 107. The proximal connector 104 may be configured to detachably couple the occlusion device 100 to a delivery system, and the distal connector 106 may be configured to couple a lead-in member to the mesh structure 102, as described in greater detail below with respect to FIGS. 2A-3B.

The mesh ribbon 107 can be formed of a tubular mesh that has been flattened along its longitudinal axis such that opposing portions of the sidewall are pressed against one another and/or into close proximity with one another. In some embodiments, the mesh ribbon 107 is formed of a flattened tubular braid. The braid may be formed of a plurality of wires, at least some of which (e.g., 25% of the wires, 50% of the wires, 80% of the wires, 100% of the wires, etc.) are made of one or more shape memory and/or superelastic materials (e.g., Nitinol). In some embodiments, at least some of the plurality of wires may be drawn-filled tubes ("DFT") having a have a radiopaque core (e.g., platinum) surrounded by a shape memory alloy and/or superelastic alloy (e.g., Nitinol). In these and other embodiments, at least a portion of the wires can be made of other suitable materials.

In some embodiments, the mesh ribbon 107 includes a plurality of band portions 142, 144, 146 positioned along its longitudinal axis L, and one or more bend portions 112 individually positioned between adjacent band portions 142, 144, 146 along the longitudinal axis L. The first, second, and third band portions 142, 144, 146 may be configured to form the first, second, and third bands 122, 124, 126, respectively, when the mesh structure 102 is in the expanded state. For example, as shown in FIGS. 1A and 1B, the mesh ribbon 107 may include a first band portion 142, a second band portion 144 distal of the first band portion 142 along the longitudinal axis L, and a third band portion 146 distal of the second band portion 144 along the longitudinal axis L. When the mesh structure 102 is in an expanded state, the first band portion 142 may curve around a first axis (coming out of the page) to form the first band 122, the second band portion 144 may curve around the second axis A2 to form the second band 124, and the third band portion 146 may curve around a third axis A3 to form the third band 126.

The occlusion device 100 is configured to be positioned in a compressed or low-profile state within a delivery catheter (e.g., a microcatheter) so that the distal end 102b of the mesh structure 102 is closest to the distal opening of the catheter and thus will be released from the delivery catheter first. Accordingly, the third band 126 deploys first from the delivery catheter, followed by the second band 124 and the first band 122. As a result, the second band 124 expands within an interior region defined by the already-expanded third band 126, and the first band 122 expands within an interior region defined by the already-expanded second band 124. Thus, when the mesh structure 102 is in an expanded configuration positioned within the aneurysm, the second band 124 is positioned radially inward of the third band 126, and the first band 122 is positioned radially inward of the second band 124. Even if one of the bands 122, 124, 126 is positioned radially inwardly of another of the bands 122, 124, 126 in the expanded configuration, when the mesh structure 102 is expanded within an aneurysm, any radially inward band may still contact and conform to the inner surface of the aneurysm along its non-overlapping regions, especially if the diameter of the mesh structure 102 in the expanded, relaxed state is greater than that of the aneurysm. In some embodiments, when the mesh structure 102 is in an expanded state, an outer surface of the second band 124 contacts an inner surface of the third band 126 at the corresponding overlapping regions, and an outer surface of the first band 122 contacts an inner surface of the second band 124 at the corresponding overlapping regions.

Because the bands 122, 124, 126 are oriented along different planes, the bands 122, 124, 126 overlap one another along their respective circumferences, thereby forming a plurality of overlapping regions in which the porosity of the mesh structure 102 is less than it is at the non-overlapping regions of the mesh structure 102. For example, as shown in FIG. 1A, the mesh structure 102 may include six overlapping regions (e.g., 132, 134, 136, 138, 140, and 142). Depending on the number of the bands and width of the bands, the mesh structure 102 may include more or fewer overlapping regions (e.g., two overlapping regions, eight overlapping regions, etc.). The occlusion device 100 may be configured to be positioned within the aneurysm so that at least one of the overlapping regions is positioned over all or a portion of the neck of the aneurysm, thereby preventing egress of the device 100 into the parent vessel, and also disrupting the flow of blood into the aneurysm. Even if a single overlapping region covers only a portion of the aneurysm neck, the portions of the bands adjacent that overlapping region collectively provide complete or near complete neck coverage.

In some embodiments, for example as shown in FIG. 1A, when the device 100 is in the expanded state, the side edges 110a, 110b of each of the bands are spaced apart from the side edges of the other bands along at least a portion of their circumferential lengths such that the device includes openings 130 at its outer surface. In some embodiments, when the device 100 is in the expanded state, the device 100 may be configured such that the side edges 110a, 110b contact one another along at least a portion of their circumferential lengths and/or overlap one another along at least a portion of their circumferential lengths such that the bands together define a continuous outer surface of the three-dimensional shape formed by the bands (such as a sphere).

Each of the bands 122, 124, 126 may be a closed band (e.g., circumscribes a closed shape) (shown schematically in FIGS. 1C and 1D) or an open band (e.g., circumscribes an open shape) (shown schematically in FIG. 1E). For example, as shown in FIG. 1C, in some embodiments the third band portion 146 may curve 360 degrees around the third axis A3 (coming out of the page in FIG. 1C) such that the proximal end 146a of the third band portion 146 comes back around and meets the distal end 146b of the third band portion 146, thereby closing the loop and forming a closed band. As illustrated by FIG. 1D, in some embodiments the third band portion 146 may wrap around the third axis A3 more than 360 degrees such that it overlaps itself (i.e., the proximal end 146a extends circumferentially beyond the distal end 146b) along at least a portion of the circumference of the band 126, thereby forming a closed band. As illustrated by FIG. 1E, in some embodiments the third band portion 146 may curve around the third axis A3 less than 360 degrees (e.g., 330 degrees, 300 degrees, 280 degrees, 260 degrees, 230 degrees, 180 degrees, etc.) such that the proximal end 146a of the third band portion 146 does not meet the distal end 146b, thereby forming an open band. The foregoing description of the "closed" and "open" configurations of the third band 126/third band portion 146 also applies to the "closed" and "open" configurations of the first band 122/first band portion 142 and the second band 124/second band portion 144. In some embodiments, all of the bands 122, 124, 126 may be closed bands, and in some embodiments all of the bands 122, 124, 126 may be open bands. In some embodiments, at least one of the bands 122, 124, 126 is an open band and at least one of the bands 122, 124, 126 is a closed band. In some embodiments, it may be beneficial to include at least one open band as such a configuration decreases the overall length of the mesh ribbon 107 (thus making the occlusion device 100 easier to deliver through a catheter to the aneurysm) and/or frees up some of the length of the mesh ribbon 107 that can instead be used for additional bands or turns of the mesh.

The bands 122, 124, 126/band portions 142, 144, 146 can have the same or different widths w (i.e., distance between the side edges 110a, 110b) as the other bands/band portions. As shown in FIGS. 1A and 1B, each of the bands 122, 124, 126 may have tapered proximal and distal ends and a generally constant width therebetween. In some embodiments, the bands/band portions do not have any tapered regions and maintain a generally constant width along their entire respective lengths. In some embodiments, one or more of the bands/band portions have a width w that varies along its respective length.

As shown in FIGS. 1A and 1B, adjacent bands/band portions may be coupled to one another via the bend portions. In those embodiments where the bands 122, 124, 126 are formed of a single mesh ribbon, the bend portions can be narrowed regions of the mesh ribbon 107 that have been heat set to form a predetermined bend when the mesh structure 102 is in the expanded state. For example, in some embodiments the first band 122/first band portion 142 may be coupled to the second band 124/second band portion 144 by a proximal narrowed region 123, and the second band 124/second band portion 144 may be coupled to the third band 126/third band portion 146 by a distal narrowed region 125. At least when the mesh structure 102 is in the expanded, relaxed state, each of the narrowed regions 123, 125 can have a width that is less than a width w of each of the band/band portions. In those embodiments where the bands/band portions are formed of separate, discrete mesh ribbons, the bend portions can comprise separate coupling elements that link the ends of adjacent bands/band portions (such as the articulation joints shown in FIGS. 4B and 7B).

Referring to FIG. 1A, when the mesh structure 102 is in an expanded state, each of the bands 122, 124, 126 may be centered about a different axis. For example, the narrowed regions 123 and 125 are heat set to form a predetermined bend in the mesh ribbon 107 in the expanded configuration that positions the bands 122, 124, 126 at a predetermined angle relative to one another. In some embodiments, such as that shown in FIG. 1A, the individual axes of the bands 122, 124, 126 may be perpendicular to one another.

In some embodiments the occlusion device 100 may optionally include a soft, curved lead-in member 108 coupled to the distal end portion 102b of the mesh structure 102 via the distal connector 106. The lead-in member 108 may have a curved shape in a deployed configuration. For example, the lead-in member 108 initially extends distally with respect to the mesh structure 102 (e.g., from the distal connector 106) then curves proximally. Because the lead-in member 108 is the first portion of the occlusion device 100 that exits the delivery catheter and contacts the aneurysm wall, the soft material and/or curved shape of the lead-in member 108 reduces or eliminates stress on the aneurysm wall when delivering the occlusion device 100 to the aneurysm sac. In some embodiments the lead-in member 108 can be generally straight and/or have other atraumatic yet sufficiently resilient configurations. In some embodiments, the lead-in member 108 is a curled mesh (e.g., a braid) that is coupled to the distal connector 106. The curled mesh can be integral with the mesh that forms the mesh structure 102, or the curled mesh can be a separate mesh. In some embodiments, the lead-in member 108 is a separate, coiled tube (e.g., a radiopaque coil) that is coupled to the distal connector 106. In some embodiments, the lead-in member 108 can be formed integrally or monolithically with the occlusion device 100. In yet other embodiments, the occlusion device 100 does not include a lead-in member 108 and the distal portion of the occlusion device 100 is comprised solely of the distal connector 106 and/or distal end portion 102b of the mesh structure 102.

In some embodiments, the stiffness of the mesh structure 102 and/or occlusion device 100 is generally constant along its longitudinal axis L. In some embodiments, the stiffness of the mesh structure 102 and/or occlusion device 100 varies along its longitudinal axis L. For example, the stiffness of one or more portions of the mesh ribbon 107 and/or mesh structure 102 can be different than other portions of the mesh ribbon 107 and/or mesh structure 102 by varying one or more parameters such as the materials, porosity, thickness, braid count (if applicable), and braid pitch (if applicable) in the individual portions. For example, for the mesh ribbon 107 shown in FIGS. 1A and 1B, it may be desirable for the more distal first band portion 146 comprising the outermost portion of the mesh structure 102 to have a first stiffness for framing the aneurysm, and the more proximal first and second band portions 142, 144 comprising the inner mesh structures to have a second stiffness less than the first stiffness so that the first and second bands 124, 122 are more flexible than the larger third band 126 for packing the aneurysm. Moreover, it may be desirable for the third band portion 146 to be relatively stiffer than the more proximal first and second band portions 142, 144 since, once the occlusion device 100 is positioned within the aneurysm, the stiffness will enhance the anchoring and structural integrity of the first band 146.

To enhance visibility of the occlusion device 100 and/or mesh structure 102 during delivery to the aneurysm and/or subsequent to implantation within the aneurysm, the occlusion device 100 may optionally include a flexible member (not shown), such as a radiopaque element (e.g., a platinum coil), that extends along and/or within at least a portion of the length of the mesh structure 102. The proximal and distal ends of the flexible member are coupled to the proximal and distal end portions 102a, 102b, respectively, of the mesh structure 102 and/or the proximal and distal connectors 104, 106, respectively (e.g., directly or via a suture). In other embodiments, only one end of the flexible member is connected to one of the proximal connector 104 or the distal connector 106.

2.0 Methods of Use

Figure 2A:
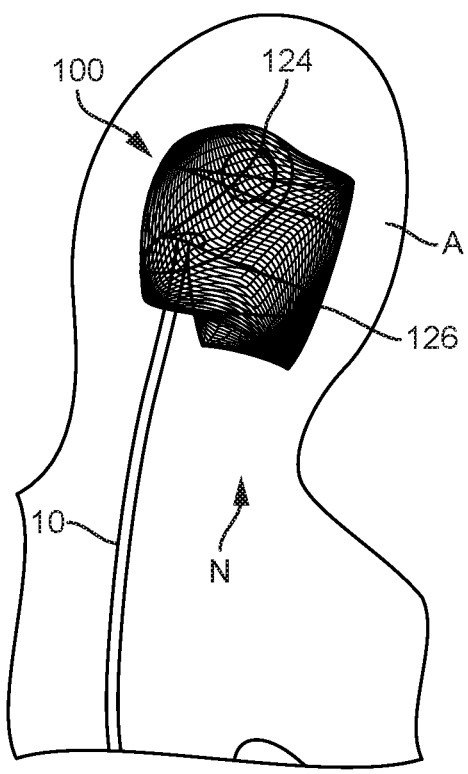
FIGS. 2A and 2B are fluoroscopic images showing a method of deploying an occlusion device within a tall aneurysm in accordance with some embodiments of the present technology.
Figure 2B:
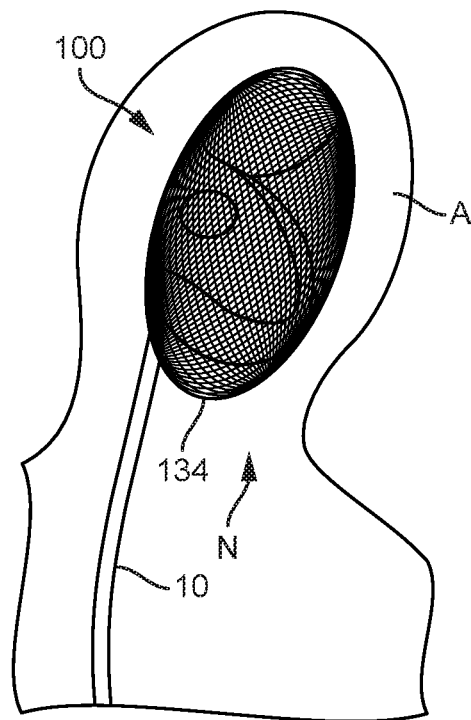
Figure 3A:
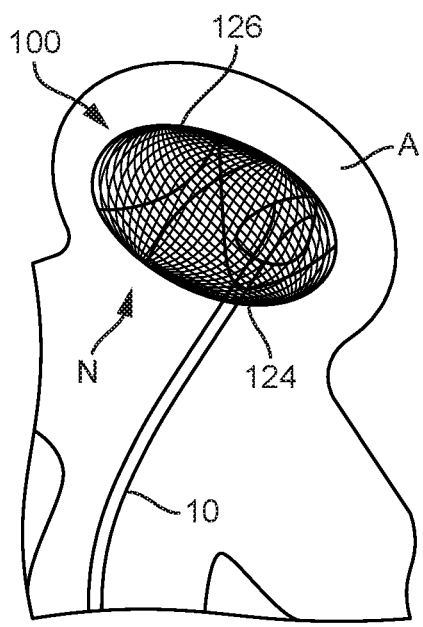
FIGS. 3A and 3B are fluoroscopic images showing a method of deploying an occlusion device within a wide aneurysm in accordance with some embodiments of the present technology.
Figure 3B:
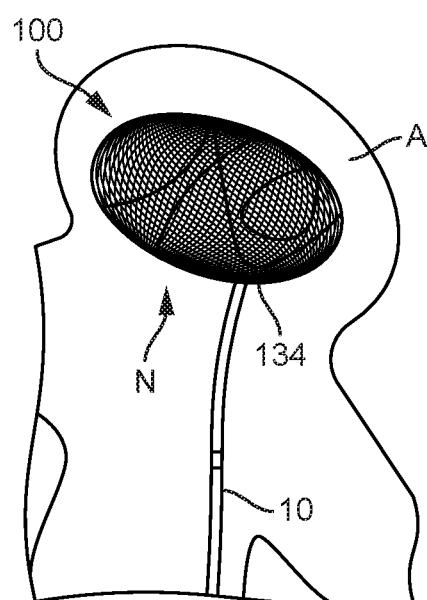

In use, the occlusion device 100 is intravascularly delivered to a location within a blood vessel lumen L adjacent a target aneurysm A in a low-profile configuration (not shown) within a delivery catheter 10. The distal portion of the delivery catheter 10 is then advanced through the neck N of the aneurysm A to an interior region of the aneurysm A. As shown in FIG. 2A, the occlusion device 100 is then deployed by pushing the occlusion device 100 distally through the distal opening of the delivery catheter 10 towards the inner wall of the aneurysm A. The third band portion 146 exits the delivery catheter 10 first and, as it's deployed, the third band portion 146 curves around the curved inner surface of the aneurysm A until forming the third band 126. The distal narrowed region 125 deploys next and assumes a first predetermined bend that directs the following second band portion 144 to curve around the aneurysm wall about an axis that is perpendicular to the central axis of the third band 126, thereby forming the second band 124. The proximal narrowed region 123 deploys next and assumes a second predetermined bend that directs the following first band portion 142 to curve around the aneurysm wall about an axis that is perpendicular to a central axis of the third band 126 and a central axis of the second band 124, thereby forming the first band 122. As shown in FIG. 2B, at least one of the overlapping regions is positioned over all or a portion of the neck N, thereby preventing egress of the device 100 into the parent vessel, and also disrupting the flow of blood into the aneurysm A. Unlike conventional devices, the occlusion device 100 is configured to treat a range of aneurysm geometries without additional anchoring devices. For example, FIGS. 2A and 2B show the occlusion device 100 anchored within and conformed to a tall aneurysm geometry (aspect ratio≤1:2), and FIGS. 3A and 3B show the occlusion device 100 anchored within and conformed to a wide aneurysm geometry (aspect ratio≥2:1).

3.0 Additional Embodiments

Figure 4A:
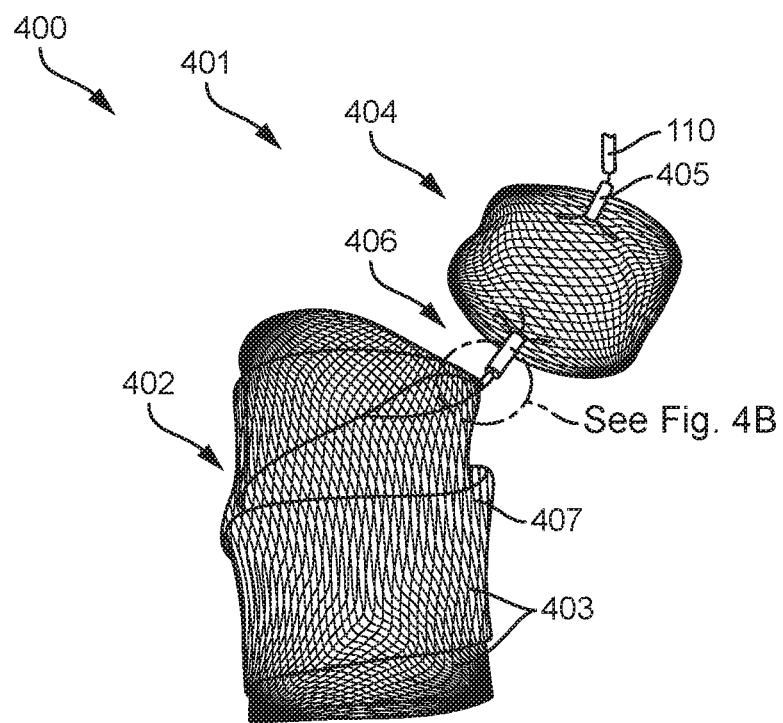
FIG. 4A is an occlusion device in a deployed, relaxed state outside of an aneurysm according to some embodiments of the present technology.
Figure 4B:
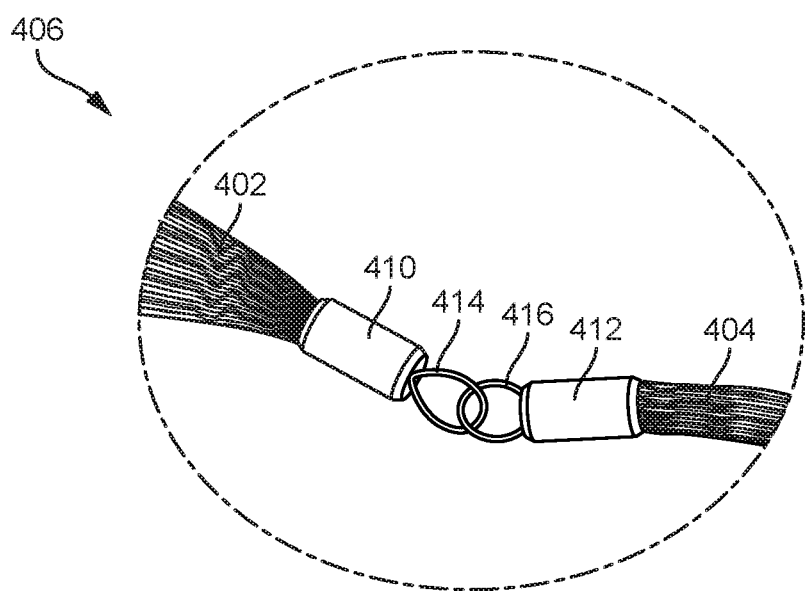
FIG. 4B is an enlarged view of an articulation joint of the occlusion device shown in FIG. 4A according to some embodiments of the present technology.

FIGS. 4A-9B show several embodiments of occlusion devices configured in accordance with the present technology. For example, FIG. 4A illustrates an occlusion device 400 (or "device 400") comprising a mesh structure 401 having an expanded, relaxed state in which it includes a globular (e.g., cylindrical, spherical, ball-shaped, barrel-shaped, etc.) first portion 404 and a helical second portion 402. In some embodiments, such as that shown in FIG. 4A, the first and second portions 404, 402 can be separate meshes coupled via a coupling element 406. In some embodiments, the first and second portions 404, 402 can be formed from a single, continuous mesh such that the first and second portions 404, 402 are integrally connected with one another. In some embodiments, one or both of the first and second portions 404, 402 are formed of a braided material.

The globular first portion 404 can have a proximal connector 405 at its proximal end and a distal connector 412 at its distal end. The proximal connector 405 is configured to detachably couple the occlusion device 400 to a delivery device (such as delivery member 110). As such, the helical second portion 402 is configured to be delivered first to the aneurysm, followed by the first portion 404. The distal connector 412 may include a loop 416 extending therefrom and configured to engage and/or interlock with a loop 414 extending from a proximal connector 410 at a proximal end of the second portion 402. The interlocking loops 414, 416 allow the second portion 402 to bend and rotate (to some extent) relative to the first portion 404 (and vice versa), thus enabling the device 400 to adapt to the shape and size of the aneurysm.

The helical second portion 402 can be formed of a mesh ribbon 407 wrapped about an axis a plurality of times to form a plurality of mesh turns 403 (only two labeled for ease of illustration) in the expanded configuration. The mesh turns 403 may overlap one another along their edges. The mesh ribbon 407 can be formed of a tubular mesh (e.g., a braided tube) that has been flattened along its longitudinal axis such that opposing portions of the sidewall are pressed against one another and/or into close proximity with one another. In some embodiments, the mesh ribbon 407 is formed of a flattened tubular braid. The braid may be formed of a plurality of wires, at least some of which (e.g., 25% of the wires, 50% of the wires, 80% of the wires, 100% of the wires, etc.) are made of one or more shape memory and/or superelastic materials (e.g., Nitinol). In some embodiments, at least some of the plurality of wires may be drawn-filled tubes ("DFT") having a have a radiopaque core (e.g., platinum) surrounded by a shape memory alloy and/or superelastic alloy (e.g., Nitinol). In these and other embodiments, at least a portion of the wires can be made of other suitable materials.

Figure 5A:
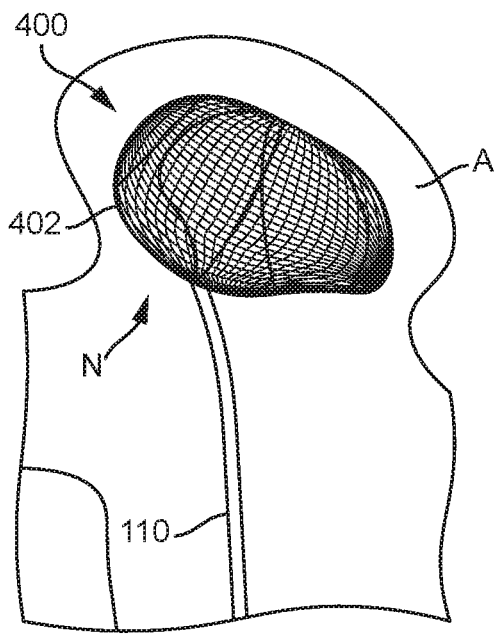
FIGS. 5A and 5B are fluoroscopic images showing a method of deploying an occlusion device within a wide aneurysm in accordance with some embodiments of the present technology.
Figure 5B:
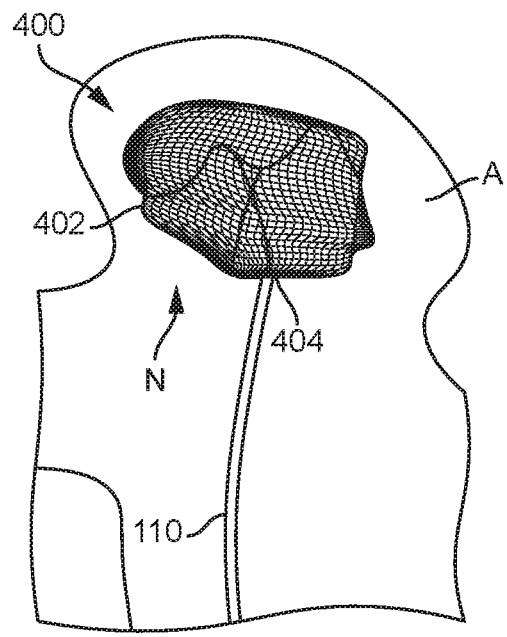
Figure 6A:
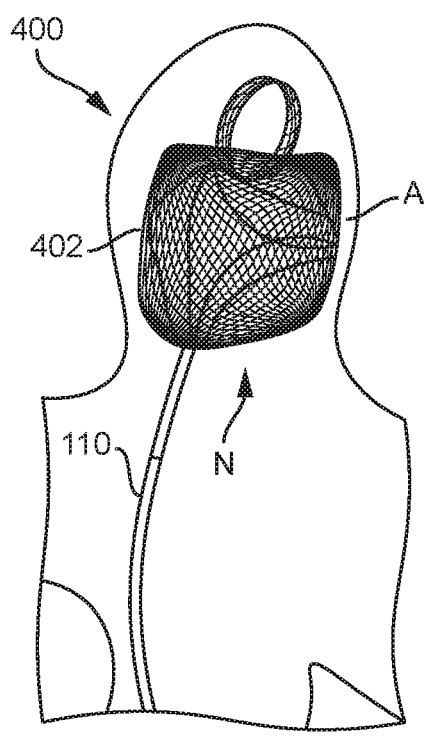
FIGS. 6A and 6B are fluoroscopic images showing a method of deploying an occlusion device within a tall aneurysm in accordance with some embodiments of the present technology.
Figure 6B:
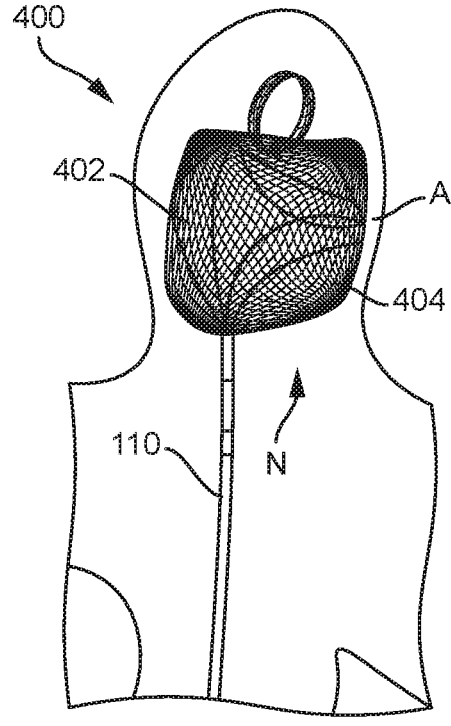

FIGS. 5A and 5B are fluoroscopic images the occlusion device 400 being deployed within a wide aneurysm in accordance with some embodiments of the present technology, and FIGS. 6A and 6B are fluoroscopic images showing the occlusion device 400 being deployed within a tall aneurysm in accordance with some embodiments of the present technology. As shown, the helical second portion 402 may be deployed first within the aneurysm, followed by the first portion 404. The globular first portion 404 can press outwardly against the aneurysm wall and help anchor the first portion 402 within the aneurysm. The globular first portion 404 can also fill any gaps at the neck of the aneurysm left by the second portion 402.

Figure 7A:
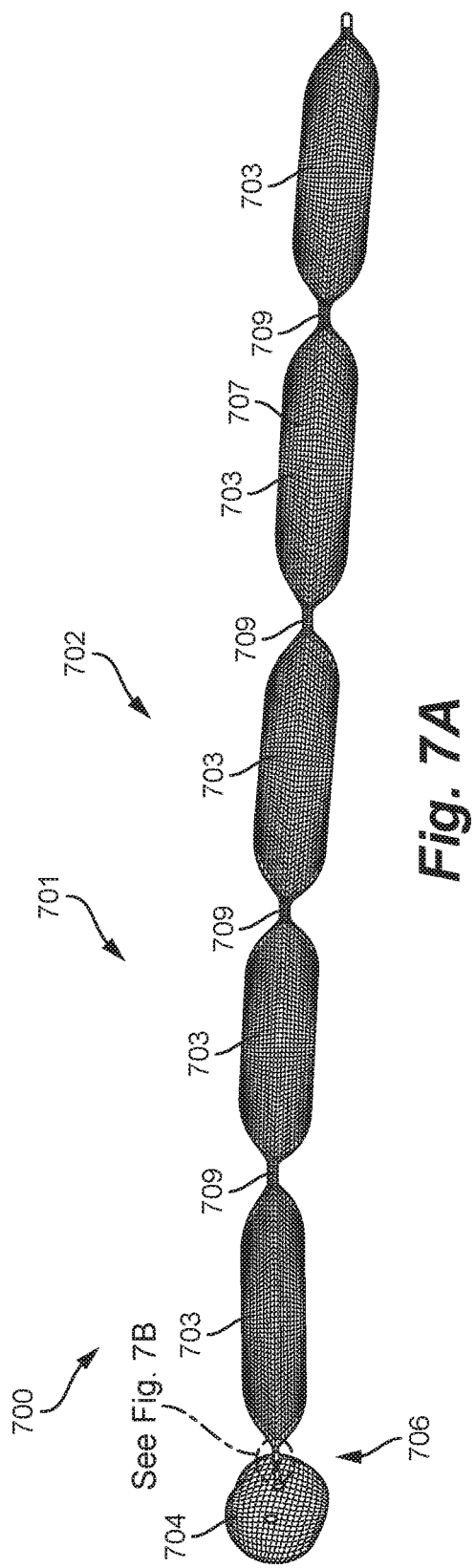
FIG. 7A is an occlusion device in a deployed, relaxed state outside of an aneurysm according to some embodiments of the present technology.
Figure 7B:
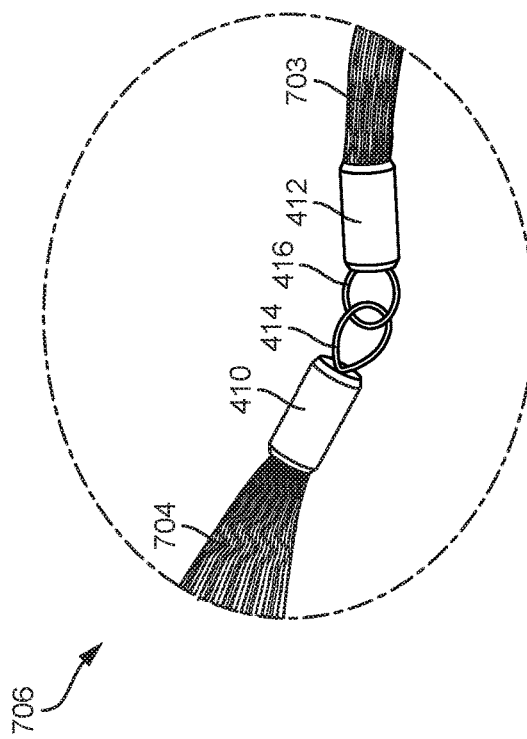
FIG. 7B is an enlarged view of an articulation joint of the occlusion device shown in FIG. 7A according to some embodiments of the present technology.

FIG. 7A illustrates an occlusion device 700 (or "device 700") comprising a mesh structure 701 having an expanded, relaxed state in which it includes a globular (e.g., cylindrical, spherical, ball-shaped, barrel-shaped, etc.) first portion 704 and a second portion 702. In some embodiments, such as that shown in FIG. 4A, the first and second portions 704, 702 can be separate meshes coupled via a coupling element 406. In some embodiments, the first and second portions 704, 702 can be formed from a single, continuous mesh such that the first and second portions 704, 702 are integrally connected with one another. In some embodiments, one or both of the first and second portions 704, 702 are formed of a braided material.

The globular first portion 704 can have a proximal connector 405 at its proximal end and a distal connector 412 at its distal end. The proximal connector 405 is configured to detachably couple the occlusion device 700 to a delivery device (such as delivery member 110). The distal connector 412 may include a loop 416 extending therefrom and configured to engage and/or interlock with a loop 414 extending from a proximal connector 410 at a proximal end of the second portion 702. The interlocking loops 414, 416 allow the second portion 702 to bend and rotate (to some extent) relative to the first portion 404 (and vice versa), thus enabling the device 700 to adapt to the aneurysm cavity.

The second portion 702 can include a plurality of rectangular regions 703 separated by flexible, narrowed bend regions 709. The second portion 702 may be formed of a mesh ribbon 707. The mesh ribbon 707 can be formed of a tubular mesh (e.g., a braided tube) that has been flattened along its longitudinal axis such that opposing portions of the sidewall are pressed against one another and/or into close proximity with one another. In some embodiments, the mesh ribbon 707 is formed of a flattened tubular braid. The braid may be formed of a plurality of wires, at least some of which (e.g., 25% of the wires, 50% of the wires, 80% of the wires, 100% of the wires, etc.) are made of one or more shape memory and/or superelastic materials (e.g., Nitinol). In some embodiments, at least some of the plurality of wires may be drawn-filled tubes ("DFT") having a have a radiopaque core (e.g., platinum) surrounded by a shape memory alloy and/or superelastic alloy (e.g., Nitinol). In these and other embodiments, at least a portion of the wires can be made of other suitable materials.

Figure 8A:
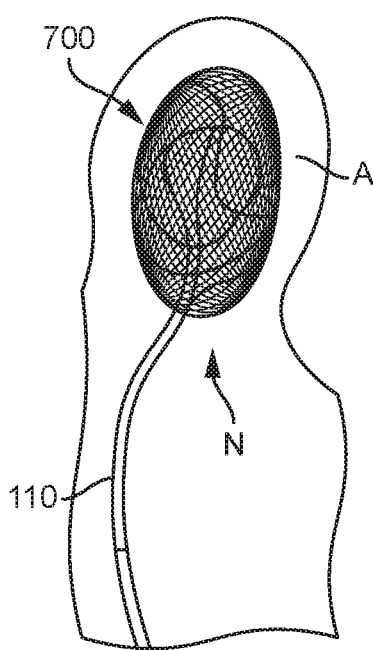
FIGS. 8A and 8B are fluoroscopic images showing a method of deploying an occlusion device within a wide aneurysm in accordance with some embodiments of the present technology.
Figure 8B:
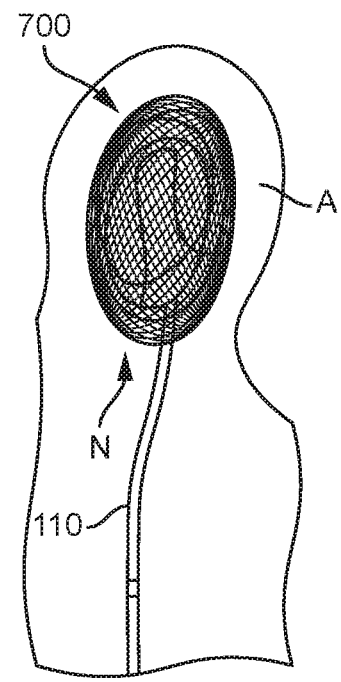
Figure 9A:
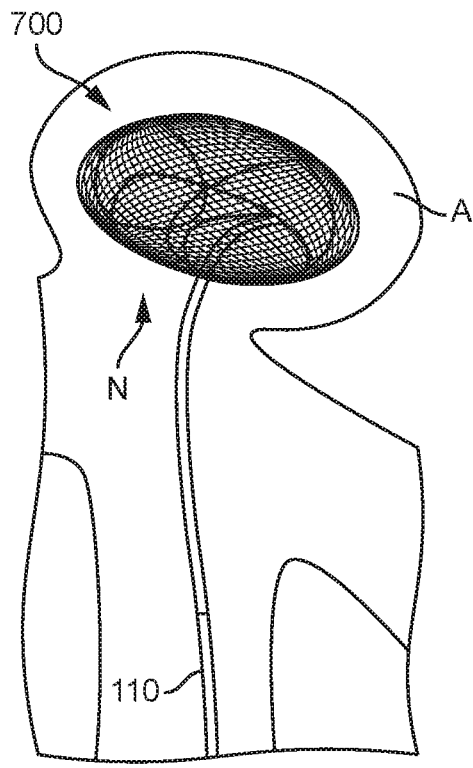
FIGS. 9A and 9B are fluoroscopic images showing a method of deploying an occlusion device within a wide aneurysm in accordance with some embodiments of the present technology.
Figure 9B:
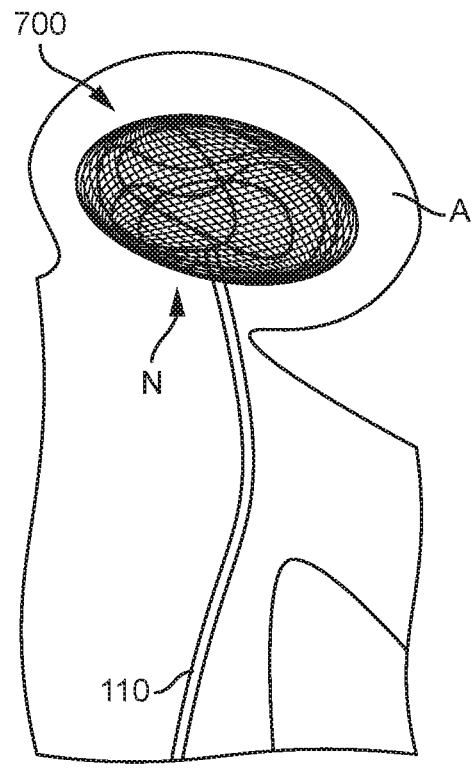

FIGS. 8A and 8B are fluoroscopic images showing the occlusion device 700 being deployed within a tall aneurysm in accordance with some embodiments of the present technology, and FIGS. 9A and 9B are fluoroscopic images showing the occlusion device 700 being deployed within a wide aneurysm in accordance with some embodiments of the present technology. As shown, the second portion 702 may be deployed first within the aneurysm, followed by the first portion 704. The globular first portion 704 can press outwardly against the aneurysm wall and help anchor the first portion 702 within the aneurysm. The globular first portion 704 can also fill any gaps at the neck of the aneurysm left by the second portion 702.

5.0 Conclusion

Although many of the embodiments are described above with respect to devices, systems, and methods for treating a cerebral aneurysm, other applications and other embodiments in addition to those described herein are within the scope of the technology. For example, the occlusion devices, systems, and methods of the present technology can be used to treat any vascular defect and/or fill or partially fill any body cavity or lumen or walls thereof. Additionally, several other embodiments of the technology can have different states, components, or procedures than those described herein. It will be appreciated that specific elements, substructures, advantages, uses, and/or other features of the embodiments described can be suitably interchanged, substituted or otherwise configured with one another in accordance with additional embodiments of the present technology. A person of ordinary skill in the art, therefore, will accordingly understand that the technology can have other embodiments with additional elements, or the technology can have other embodiments without several of the features shown and described above.

We claim:

1. An occlusive device for treating an aneurysm, wherein a neck of the aneurysm opens to a blood vessel, the device comprising:
    a first elongated mesh having a low-profile state for intravascular delivery to the aneurysm and an expanded state in which the first elongated mesh is curved about a first axis to form a first band, the first elongated mesh having a length and a generally constant width along the entire length; and
    a second elongated mesh having a low-profile state for intravascular delivery to the aneurysm and an expanded state in which the second elongated mesh is curved about a second axis to form a second band, wherein a distal end of the second elongated mesh is coupled to a proximal end of the first elongated mesh;
    wherein the second band is positioned radially inward of the first band such that the device includes first and second overlap regions in which the first band overlaps the second band, and wherein the first and second overlap regions are spaced apart from one another along a circumference of the first band.

2. The device of claim 1, wherein the first and second elongated meshes are self-expanding.

3. The device of claim 1, wherein the first and second bands together bound a generally spherical shape, and wherein the first and second bands conform to an interior geometry of the aneurysm when the device is positioned within the aneurysm.

4. The device of claim 1, wherein the device is configured to be positioned in the aneurysm in an expanded state such that the first or second overlap region is positioned at the neck of the aneurysm, thereby substantially covering the neck and reducing blood flow through the neck from a parent vessel.

5. The device of claim 1, wherein the first axis is generally perpendicular to the second axis.

6. The device of claim 1, wherein at least one of the first elongated mesh and the second elongated mesh is a braid.

7. The device of claim 1, wherein at least one of the first elongated mesh and the second elongated mesh is a flattened tubular braid.

8. The device of claim 1, wherein a proximal end of the first elongated mesh is configured to be detachably coupled to an elongated delivery member.

9. An occlusive device for treating an aneurysm, wherein a neck of the aneurysm opens to a blood vessel, the device comprising:
    a first elongated mesh strip having a low-profile state for intravascular delivery to the aneurysm and an expanded state in which the first elongated mesh strip is curved about a first axis to form a first band encircling at least a portion of a first opening;
    a second elongated mesh strip having a low-profile state for intravascular delivery to the aneurysm and an expanded state in which the second elongated mesh strip is curved about a second axis to form a second band encircling at least a portion of a second opening, wherein a distal end of the second elongated mesh strip is coupled to a proximal end of the first elongated mesh strip; and
    a third elongated mesh strip having a low-profile state for intravascular delivery to the aneurysm and an expanded state in which the third elongated mesh strip is curved about a third axis to form a third band encircling at least a portion of a third opening, wherein a distal end of the third elongated mesh strip is coupled to a proximal end of the second elongated mesh strip;

wherein, when the device is in an expanded, unconstrained state, the first, second, and third openings are aligned with first, second, and third planes, respectively, and the first second and third planes are perpendicular to one another, and wherein the first strip has a length, and wherein the first elongated mesh strip has a generally constant width along the length.

10. The device of claim 9, wherein:
the first, second, and third bands together bound a predetermined, three-dimensional shape,
the first elongated mesh has first longitudinal side edges,
the second elongated mesh is bound by second longitudinal side edges,
the third elongated mesh is bound by third longitudinal side edges, and
when the device is in the expanded state, the first, second, and third side edges are spaced apart from one another along at least a portion of their circumferential lengths such that the device includes openings at its outer surface.

11. The device of claim 9, wherein:
the first, second, and third bands together bound a predetermined, three-dimensional shape,
the first elongated mesh has first longitudinal side edges,
the second elongated mesh is bound by second longitudinal side edges, and
when the device is in the expanded state, the first and the second side edges contact one another along at least a portion of their circumferential lengths and/or overlap one another along at least a portion of their circumferential lengths such that the first, second, and third bands define a continuous outer surface of the three-dimensional shape.

12. The device of claim 9, wherein, when the device is in an expanded, unconstrained state, the third band is radially inward of the second band, and the second band is radially inward of the first band.

13. The device of claim 12, wherein, in the expanded state, the first band is an open band such that when the first band is viewed in cross section, it does not form a closed shape.

14. The device of claim 12, wherein, in the expanded state, the second band is an open band such that when the second band is viewed in cross section, it does not form a closed shape.

15. The device of claim 12, wherein, in the expanded state, the third band is an open band such that when the third band is viewed in cross section, it does not form a closed shape.

16. The device of claim 12, wherein, in the expanded state, the first band is a closed band such that when the first band is viewed in cross section, it forms a closed shape.

17. The device of claim 12, wherein, in the expanded state, the second band is a closed band such that when the second band is viewed in cross section, it forms a closed shape.

18. The device of claim 12, wherein, in the expanded state, the third band is a closed band such that when the third band is viewed in cross section, it forms a closed shape.

19. A method for treating an aneurysm with an occlusive device including a first elongated mesh and a second elongated mesh, wherein a neck of the aneurysm opens to a blood vessel, the method comprising:
pushing the first elongated mesh distally from a delivery catheter into an interior region of the aneurysm, the first elongated mesh having a length and a generally constant width along the length, wherein pushing the first elongated mesh distally includes curving the first elongated mesh back on itself to form a first band that expands against and conforms to an inner surface of the aneurysm wall;
pushing a second elongated mesh distally from the delivery catheter into the interior region of the aneurysm, wherein a distal end of the second elongated mesh is coupled to a proximal end of the first elongated mesh, and wherein pushing the second elongated mesh distally includes curving the second elongated mesh back on itself to form a second band that expands against and conforms to the inner surface of the aneurysm wall, wherein the first and second bands intersect at first and second overlap regions when the device is in an expanded state; and
positioning the device within the aneurysm such that the first or second overlap region is positioned at the neck of the aneurysm, thereby substantially covering the neck and reducing blood flow from a parent vessel through the neck.

20. The method of claim 19, wherein the first elongated mesh is pushed distally from the delivery catheter before the second elongated mesh is pushed distally from the delivery catheter.

21. The method of claim 19, wherein:
curving the first elongated mesh back on itself to form a first band includes curving the first elongated mesh around a first axis; and
curving the second elongated mesh back on itself to form a second band includes curving the second elongated mesh around a second axis different than the first axis.

22. The method of claim 21, wherein the first axis is perpendicular to the second axis.

23. The method of claim 19, wherein the first and second elongated meshes are formed of a single, continuous elongated mesh.

24. The method of claim 19, further comprising pushing a third elongated mesh distally from the delivery catheter into the interior region of the aneurysm, wherein pushing the third elongated mesh distally includes curving the third elongated mesh back on itself to form a third band that expands against and conforms to the inner surface of the aneurysm wall.

* * * * *

UNITED STATES PATENT AND TRADEMARK OFFICE
CERTIFICATE OF CORRECTION

PATENT NO. : 11,304,700 B2
APPLICATION NO. : 16/738968
DATED : April 19, 2022
INVENTOR(S) : Rosqueta et al.

It is certified that error appears in the above-identified patent and that said Letters Patent is hereby corrected as shown below:

In the Claims

In Column 17, in Claim 9, Line 4, after "first" insert -- , --.

Signed and Sealed this
Thirty-first Day of May, 2022

*Katherine Kelly Vidal*

Katherine Kelly Vidal
*Director of the United States Patent and Trademark Office*